United States Patent [19]

Nagano et al.

[11] Patent Number: 5,081,116
[45] Date of Patent: Jan. 14, 1992

[54] CEPHALOSPORIN DERIVATIVES

[75] Inventors: Noriaki Nagano; Masato Satoh, both of Ibaraki; Masauki Komiya, Saitama; Toshio Okazaki, Ibaraki; Tetsuya Maeda; Tadao Shibanuma, both of Saitama, all of Japan

[73] Assignee: Yamanouchi Pharmaceutical Co., Ltd., Tokyo, Japan

[21] Appl. No.: 504,926

[22] Filed: Apr. 5, 1990

[30] Foreign Application Priority Data

Apr. 12, 1989 [JP] Japan .................................. 1-92615

[51] Int. Cl.$^5$ .................. C07D 501/36; A61K 31/545
[52] U.S. Cl. .................................... 514/206; 540/227; 540/226
[58] Field of Search .................. 540/226, 227; 514/206

[56] References Cited

U.S. PATENT DOCUMENTS 4,264,595  4/1981  Numata et al. ...................... 540/222

Primary Examiner—Nicholas S. Rizzo
Attorney, Agent, or Firm—Burgess, Ryan & Wayne

[57] ABSTRACT

A 7-[2-(2-amino-4-thiazolyl)-2-(hydroxyimino)-acetamido]-3-(1,3-dithiolan-2-yl)-3-cephem-4-carboxylic acid derivative is provided which can be represented by the general formula:

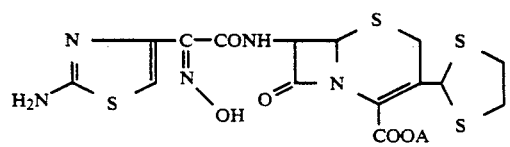

wherein A represents a hydrogen atom, a 1-acetoxyethyl group, a 1-cyclohexylacetoxyethyl group or a pivaloyloxy-methyl group.

15 Claims, No Drawings

CEPHALOSPORIN DERIVATIVES

BACKGROUND OF THE INVENTION

1. Field of the Invention

The present invention relates to cephalosporin type antimicrobial compounds excellent in oral absorption.

2. Summary of the Invention

The compounds of the present invention are 7-[2-(2-amino-4thiazolyl)-2-(hydroxyimino)acetamido]-3-(1,3-dithiolan-2-yl)-3-cephem-4-carboxylic acid derivatives represented by the following general formula:

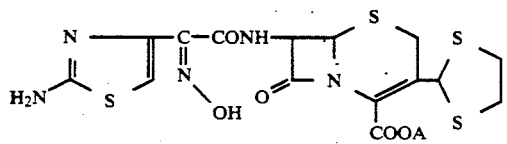

wherein A represents a hydrogen atom, a 1-acetoxyethyl group, a 1-cyclohexylacetoxyethyl group or a pivaloyloxymethyl group.

The 1-acetoxyethyl group, 1-cyclohexylacetoxyethyl group and pivaloyloxymethyl group represented by the above-described A are groups represented by

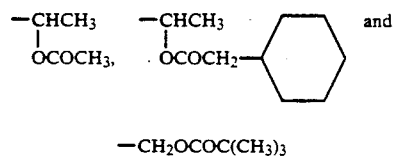

$-CH_2OCOC(CH_3)_3$ respectively.

The compounds (I) provided by the present invention are novel cephalosporin derivatives having a chemical structure wherein the 1,3-dithiolan-2-yl group is present at the position 3 of the cephalosporin nucleus and also the hydroxyimino group is substituted at the position $\alpha$ to the acetamido group at the position 7.

DESCRIPTION OF THE PREFERRED EMBODIMENTS

This compound has an excellent absorption rate from the digestive tract and exhibits a high antimicrobial activity and therefore is a cephalosporin derivative suitable for oral administration. The antimicrobial activity of the 7-[2-(2-amino-4-thiazolyl)-2-(hydroxyimino)acetamido]-3-(1,3-dithiolan-2-yl)-3-cephem-4-carboxylic acid which is such that A of the compounds of the general formula is the hydrogen atom (Compound of Example 1) is shown in Table 1.

TABLE 1

| Name of Strain | (Minimum Growth Inhibition Concentration. γ/ml) Antimicrobial Activity |
|---|---|
| Staphylococcus aureus FDA 209P JC-1 | 0.39 |
| Staphylococcus epidermidis IID 866 | 0.39 |
| Enterobacter Faecalis CAY 1104 | 3.13 |
| Escherichia coli 0-1 | 0.39 |
| Klebsiella pneumoniae ATCC 10031 | 0.78 |

Further, the absorption rate of the compound of the general formula (I) wherein A is the 1-acetoxyethyl group (Compound of Example 2) from the digestive tract is shown as follows together with the testing method therefor.

(1) Testing Method

An ether-anesthetized rat was fixed with the belly upside and a polyethylene tube was inserted into the bile-duct. The urine was collected from the same rat. After the test compound was orally administered at 50 mg/kg, urine and bile samples were collected within 0-6 hours and also within 6-24 hours. The amounts recovered in the urine and the bile within 24 hours were determined by measuring the test compound concentrations in the urine and the bile by a bioassay method using the standard solution of the test compound prepared with M/15 phosphate buffer.

(2) Test Results (Absorption Rate)

| | Recovery Rate (%) within 24 hours | | |
|---|---|---|---|
| | In the Urine | In the Bile | Total |
| Test Compound | 14.1 | 8.5 | 22.6 |

The compounds (I) of the present invention are administered as such, or administered as salts. The salts are salts with pharmacologically acceptable acids or bases. As the salts with acids, there may be mentioned inorganic acid salts such as hydrohalogenic acid salts (hydrochloric acid salts, hydrobromic acid salts etc.), sulfates etc. and salts with organic acids such as formates, acetates, fumarates, citrates etc. Further, as the salts with the bases, there are alkali metal salts, salts with organic bases and basic amino acids such as dicyclohexylamine, triethylamine, arginine, lysine etc.

The compounds of the present invention or salts thereof are mainly orally administered as tablets, capsules, syrups etc. The dosage varies depending on the graveness of the condition, the body weight etc. and is 200-3,000 mg per day for adults, and this is administered in 1 or 2 portions. The preparation of the respective formulations may be effected in the conventional manner by adding excipients, preservatives, stabilizers etc. employed in the pharmaceutical field.

PROCESS FOR THE PREPARATION

The compounds of the present invention may be produced by the process represented by the following reaction schemes:

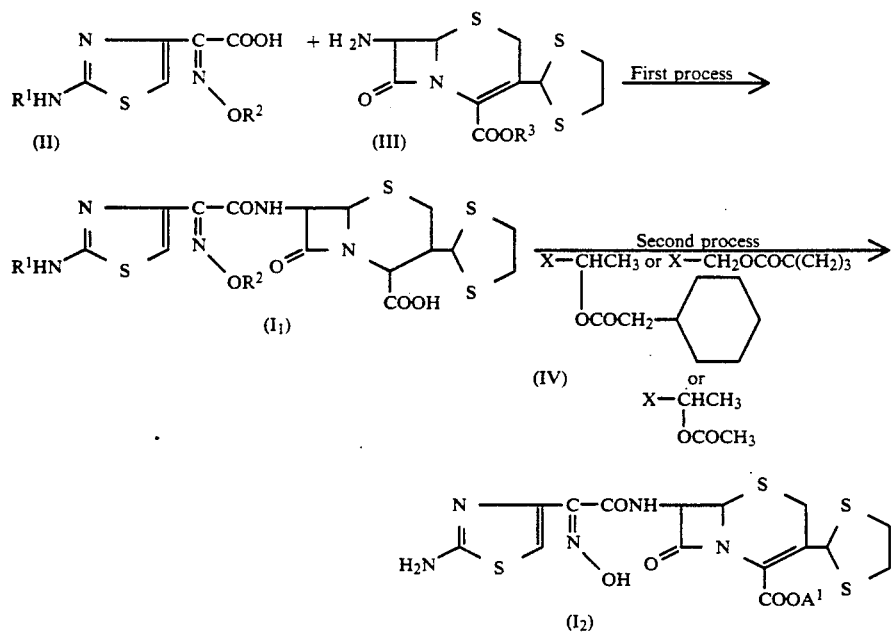

wherein $A^1$ represents a 1-acetoxyethyl group, a 1-cyclohexylacetoxyethyl group or a pivaloyloxymethyl group, $R^1$ represents a hydrogen atom or a protective group for the amino group, $R^2$ represents a hydrogen atom or a protective group for the hydroxyl group, $R^3$ represents a hydrogen atom or a protective group for the carboxyl group, and X represents a halogen atom.

The first step is a process which comprises the reaction (amidation) of an alkoxyiminothiazole acetic acid derivative represented by the general formula (II) or a reactive derivative thereof at its carboxyl group with a 7-amino-3-(1,3-dithiolan- 2-yl)cephalosporin derivative represented by the general formula (III) and thereafter the removal of the protective group for the carboxyl group, followed by, depending on the case, the removal of the protective groups for the amino group and the hydroxyl group in the product to produce the compound ($I_1$) wherein A is a hydrogen atom.

Here, as the protective group for the carboxyl group, there may be specifically mentioned protective groups which may be removed easily under mild conditions, such as a trimethylsilyl group, a benzhydryl group, a β-methylsulfonylethyl group, a phenacyl group, a p-methoxybenzyl group, a tert-butyl group, a p-nitrobenzyl group etc.

As the protective group for the amino group, there may be mentioned, for example, acyl groups such as a formyl group, an acetyl group, a propionyl group, a tertiary (abbreviated as tert or t)-butoxycarbonyl group, a methoxyacetyl group, a methoxypropionyl group, a benzyloxycarbonyl group, a p-nitrobenzyloxycarbonyl group etc., aralkyl groups such as a benzyl group, a benzhydryl group, a trityl group etc. and the like.

As the protective group for the hydroxyl group, there are a (1-methoxy-1-methyl)ethyl group, lower alkylsilyl groups such as a trimethylsilyl group etc. and the like.

The amidation reaction is generally conducted in a solvent with cooling or at room temperature. The solvent is not particularly restricted as long as it does not participate in the reaction, but as those generally employed, there may be mentioned organic solvents such as dioxane, tetrahydrofuran, ether, acetone, methyl ethyl ketone, chloroform, methylene chloride, ethylene chloride, methanol, ethanol, acetonitrile, ethyl acetate, ethyl formate, dimethylformamide, dimethylsulfoxide etc. These solvents may also be used by appropriately mixing.

The compound (II) may be used in the reaction not only as the state of a free carboxylic acid but also as a reactive derivative of the carboxylic acid. Those suitable are mixed acid anhydrides, acid halides, activated esters, activated amides, acid anhydrides, acid azides etc. When the compound (II) is used in the state of a free carboxylic acid, it is preferred to use a condensing agent such as N,N'-dicyclohexylcarbodiimide, N,N'-diethylcarbodiimide etc.

Further, depending on the kind of the reactive derivative of the carboxylic acid used, that the reaction to be conducted it is preferred for smoothly proceeding that the reaction be conducted in the presence of a base. As this base, there may be mentioned inorganic bases such as sodium bicarbonate, potassium bicarbonate, sodium carbonate, potassium carbonate etc., and organic bases such as trimethylamine, triethylamine, dimethylaniline, pyridine etc.

The removal of the protective group from the thus obtained product may be easily effected, for example, by using an acid in the case of the benzhydryl group, the p-methoxybenzyl group etc., or by contacting with water in the case of the trimethylsilyl group.

Further, the removal of the protective group for the amino group may be easily conducted by hydrolysis where the above-mentioned aralkyl group such as the trityl group or one of the various acyl groups is used as the protective group. As the acid used on this occasion, formic acid, trifluoroacetic acid, hydrochloric acid etc. are preferred.

Furthermore, it is also possible to simultaneously conduct the removal of the protective group for the carboxyl group and the protective group for the amino group. As the reaction solvent, methanol, acetone, dichloromethane, tetrahydrofuran, dimethylsulfoxide, dimethylformamide etc. may be used either singly or by appropriately mixing.

In the next place, the second step is to esterify the carboxyl group at the position 3 of the cephalosporin compound represented by the formula (I₁) obtained in the previous step by using a halogen compound (IV), The carboxyl group in the formula (I₁) compound is used not only as the free state (free carboxylic acid) but also as the state of a reactive derivative such as a salt of the carboxylic acid etc. As the halogen compound (IV), for example, 1-iodoethyl acetate, 1-bromoethyl acetate, 1-iodoethyl 1-cyclohexyl acetate, 1-bromoethyl 1-cyclohexyl acetate, iodopivaloyloxymethyl, chloropivaloyloxymethyl etc. may be used.

The esterification reaction is conducted in an appropriate solvent by using the halogen compound (IV) in an amount equimolar or excess to the compound (I₁). As the solvent, dimethylformamide, acetone, dimethylsulfoxide etc. are suitable. The reaction may easily proceed at room temperature or with cooling, but in order to promote the reaction, a base such as potassium carbonate, sodium bicarbonate etc. is added.

Thereafter, if the product obtained by the above-described process has a protecting group, this is removed by the above-described process.

The salts of the compounds of the present invention represented by the general formula (I) may be produced by using the salt of the starting material in the above-described production process, or by applying a salt-forming reaction conventionally employed in this field to the free compound produced by the above-described process.

Isolation and purification of the compounds of the present invention (I) or salts thereof may be conducted in the conventional manner, and separation and purification by extraction with organic solvents, crystallization, column chromatography etc. are employed.

EXAMPLES

Then, the compounds of the present invention and the process for the production therefor are described in more detail by giving examples.

EXAMPLE 1

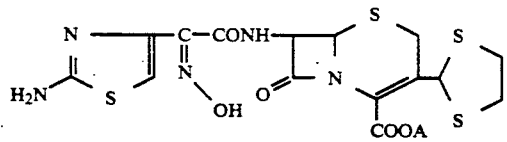

(1) 5.39 g of (Z)-2-hydroxyimino-2-(2-tritylamino-4-thiazolyl)acetic acid is suspended in 105 ml of dichloromethane, and 3.6 ml of 2-methoxypropene is added at 10° C. After stirring at room temperature for 30 minutes, the solvent is distilled off under reduced pressure. 75 ml of dichloromethane is added to the residue, 2.74 g of phosphorus pentachloride is added at −25° C., and stirred at −20° to −15° C. for 30 minutes to obtain a solution of (Z)-2-(1-methoxy-1-methyl)ethoxyimino-2-(2-tritylamino-4-thiazolyl)acetic acid chloride.

On the other hand, 3.50 g of a trifluoroacetic acid salt of 7-amino-3-(1,3-dithiolan-2-yl)-3-cephem-4-carboxylic acid is suspended in 70 ml of dichloromethane, and 4.13 ml of bis(trimethylsilyl)acetamide is added thereto at 10° C. After stirring at room temperature for 15 minutes, 3.38 ml of pyridine and the above-described acetic acid chloride solution are added successively at −65° C. After stirring at −40° to 35° C. for 30 minutes, it is poured into 350 ml of a saturated aqueous solution of monopotassium phosphate, and extracted with 100 ml of dichloromethane twice. The organic layer is washed with 50 ml of a saturated solution of monopotassium phosphate, and dried on anhydrous magnesium sulfate. The residue obtained by distilling off the solvent under reduced pressure was subjected to silica gel column chromatography, to obtain 2.63 g (yield 40%) of (Z)-3-(1,3-dithiolan-2-yl)-7-[2-(1-methoxy-1-methyl)ethoxyimino-2-(2-tritylamino-4-thiazolyl)acetamido]-3-cephem-4-carboxylic acid from the fraction with chloroform - isopropanol - formic acid (100:3:0.3).

IR Spectrum $\nu_{max}^{KBr}$ cm⁻¹; 3415, 2980, 2945, 1790, 1685, 1530, 1070, 700

NMR Spectrum (DMSO-d₆) δ(ppm); 1.19 (6H, s, CH₃×2), 3.12 (3H, s, OCH₃), 3.18 −3.48 (4H, m, 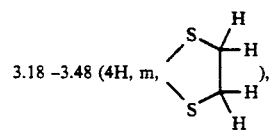 ), 3.69 (2H, s, 2-CH₂), 5.18 (1H, d, 6-CH), 5.68 (1H, dd, 7-CH), 5.99 (1H, s, 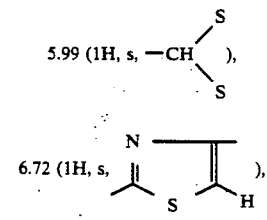 ), 6.72 (1H, s, —N=⟨ ), 7.16-7.52 (15H, m, Cφ₃), 8.84 (1H, br, s, NH), 9.47 (1H, d, CONH).

Positive Ion - FAB - Mass Spectrum; m/z 788 (M+H)⁺

(2) 9.01 g of (Z)-3-(1,3-dithiolan-2-yl)-7-[2-(1-methoxy-1-methyl)ethoxyimino-2-(2-tritylamino-4-thiazolyl)acetamido]-3-cephem-4-carboxylic acid is dissolved in 65 ml of dichloromethane, and 260 ml of 80% acetic acid is added. After stirring at 35°-40° C. for an hour, the solvent is distilled off under reduced pressure. The residue is azeotropically distilled (twice) with 200 ml of ethanol, and 485 ml of ether is added to make it a powder. The powder is recovered by filtration and dried to obtain 1.31 g (yield 92%) of (Z)-7-[2-(2-amino-4-thiazolyl)-2-(hydroxyimino)acetamido]-3-(1,3-dithiolan-2-yl)3-cephem-4-carboxylic acid.

IR Spectrum $\nu_{max}^{KBr}$ cm⁻¹; 3450, 1770, 1670, 1635, 1535.

NMR Spectrum (DMSO-d₆) δ(ppm);

3.20-3.57 (4H, m, 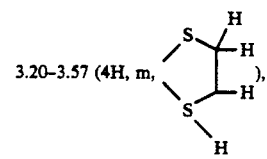 ), 3.70 (2H, s, 2-CH₂), 5.20 (1H, d, 6-CH), 5.75 (1H, dd, 7-CH), 6.01 (1H, s, 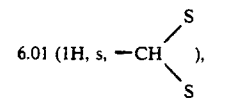), 6.68 (1H, s, 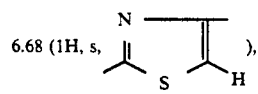), 7.12 (2H, br, s, NH$_2$), 9.45 (1H, d, CONH).
Positive Ion - FAB - Mass Spectrum; m/z 474 (M+H)$^+$

EXAMPLE 2

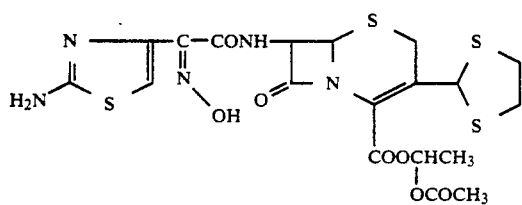

616 mg of (Z)-[7-(2-amino-4-thiazolyl)-2-(hydroxyimino)-acetamido]-3-(1,3-dithiolan-2-yl)-3-cephem-4-carboxylic acid is dissolved in 20 ml of dimethylformamide, then 100 mg of potassium carbonate is added, and thereafter 2 ml of a solution of 306 mg of 1-iodoethyl acetate in dimethylformamide is added. After stirring at −10° to 2° C. for 20 hours, the solvent is distilled off under reduced pressure, and 20 ml of ether is added to the residue to make it a powder. The powder is recovered by filtration, and subjected to silica gel column chromatography, to obtain 184 mg (yield 25%) of 1-acetoxyethyl (Z)-7-[2-(2-amino-4-thiazolyl)-2-(hydroxyimino)acetamido]-3-(1,3-dithiolan-2-yl)-3-cephem-4-carboxylate from the fraction with chloroform - methanol - formic acid (90:10:2).

IR Spectrum $\nu_{max}^{KBr}$ cm$^{-1}$; 3360, 2940, 1780, 1675, 1620, 1535, 1380, 1210, 1075, 1000, 945, 865.

NMR Spectrum (DMSO-d$_6$) δ(ppm); 1.46 (3H, dd, CH$_3$), 2.06 (3H, s, CH$_3$CO), 3.15–3.46 (4H, m, 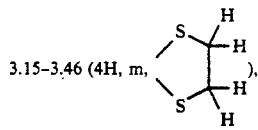), 3.70 (2H, s, 2-CH$_2$), 5.20 (1H, dd, 6-CH), 5.63–5.90 (2H, m, 7—CH, —CH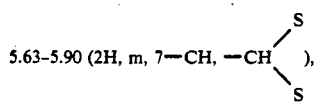), 6.63 (1H, s, 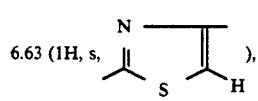), 6.90 (1H, m, COOCH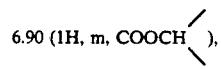), 7.09 (2H, br, s, NH$_2$), 9.43 (1H, d, CONH).

Positive Ion - FAB - Mass Spectrum; m/z 560 (M+H)$^+$

EXAMPLE 3

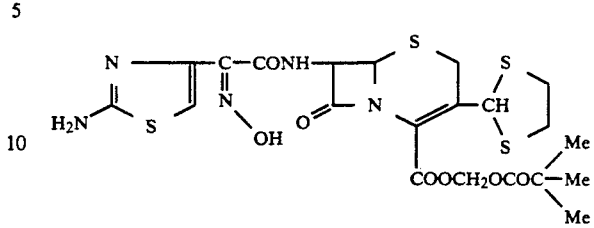

In a manner similar to that in Example 2, 113 mg of (Z)-7-[2-(2-amino-4-thiazolyl)-2-(hydroxyimino)acetamido]-3-(1,3-dithiolan-2-yl)-3-cephem-4-carboxylic acid is dissolved in 5 ml of dimethylformamide, and treated by adding 18 mg of potassium carbonate, to obtain 18 mg (yield 12.9%) of 1-pivaroyloxymethyl (Z)-7-[2-(2-amino-4-thiazolyl)-2-(hydroxyimino)acetamido]-3-(1,3-dithiolan-2-yl)-3-cephem-4-carboxylate.

IR Spectrum $\nu_{max}^{KBr}$ cm$^{-1}$; 3368, 2984, 2940, 1790, 1754, 1678, 1618, 1530, 1372, 1278, 1122, 992

NMR Spectrum (DMSO-d$_6$) δ(ppm); 1.20 (3H, s, CH$_3$), 3.50–3.52 (4H, m, 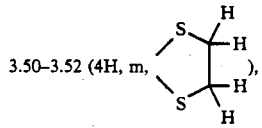), 3.77 (2H, dd, 2-CH$_2$), 5.26 (1H, d, 6-CH), 5.81–5.84 (3H, m, —COOCH$_2$—, —CH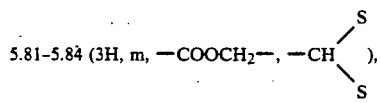), 5.95 (1H, q, 7—CH), 6.69 (1H, s, 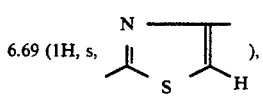), 9.46 (1H, d, —CONH—).
Positive Ion - FAB - Mass Spectrum; m/z 588 (M+H)$^+$; 610 (M+Na)$^+$

We claim:
1. A 7-[2-(2-amino-4-thiazolyl)-2-(hydroxyimino)-acetamido]-3-(1,3-dithiolan-2-yl)-3-cephem-4-carboxylic acid derivative represented by the formula:

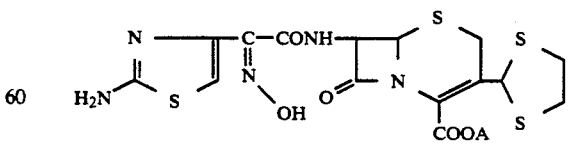

wherein A represents a hydrogen atom, a 1-acetoxyethyl group, a 1-cyclohexylacetoxyethyl group or a pivaloyloxymethyl group.

2. A compound according to claim (1) which is (Z)-7-[2-(2-amino-4-thiazolyl)-2-(hydroxyimino)-acetamido]-3-(1,3-dithiolan-2-yl)-3-cephem-4-carboxylic acid.

3. A compound according to claim (1) which is 1-acetoxyethyl (Z)-7-[2-(2-amino-4-thiazolyl)-2-(hydroxyimino)acetamido]-3-(1,3-dithiolan-2-yl)-3-cephem-4-carboxylate.

4. A compound according to claim (1) which is 1-pivaroyloxymethyl (Z)-7-[2-(2-amino-4-thiazolyl)-2-(hydroxyimino)acetamido]-3-(1,3-dithiolan-2-yl)-3-cephem-4-carboxylate.

5. A compound according to claim (1) which is 1-cylcohexylacetoxyethyl (Z)-7-[2-(2-amino-4-thiazolyl)-2-(hydroxyimino)acetamido]-3-(1,3-dithiolan-2-yl)-3-cephem-4-carboxylate.

6. A pharmaceutical composition comprised of a therapeutically effective amount of a 7-[2-(2-amino-4-thiazolyl)-2-(hydroxyimino)-acetamido]-3-(1,3-dithiolan-2-yl)-3-cephem-4carboxylic acid derivative represented by the formula:

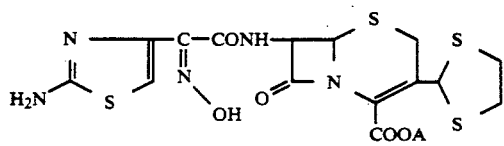

wherein A represents a hydrogen atom, a 1-acetoxyethyl group, a 1-cyclohexylacetoxyethyl group or a pivaloyloxymethyl group, and a pharmaceutically acceptable carrier.

7. The pharmaceutical composition of claim 6, wherein said derivative is (Z)-7-[2-(2-amino-4-thiazolyl)-2-(hydroxyimino)-acetamido]-3-(1,3-dithiolan-2-yl)-3-cephem-4-carboxylic acid.

8. The pharmaceutical composition of claim 6, wherein said derivative is 1-acetoxyethyl (Z)-7-[2-(2-amino-4-thiazolyl)-2-(hydroxyimino)acetamido]-3-(1,3-dithiolan-2-yl)-3-cephem-4-carboxylate.

9. The pharmaceutical composition of claim 6, wherein said derivative is 1-pivaroyloxymethyl (Z)-7-[2-(2-amino-4-thiazolyl)-2-(hydroxyimino)acetamido]-3-(1,3-dithiolan-2-yl)-3-cephem-4-carboxylate.

10. The pharmaceutical composition of claim 6, wherein said derivative is 1-cyclohexylacetoxyethyl (Z)-7-[2-(2-amino-4-thiazolyl)-2-(hydroxyimino)acetamido]-3-(1,3-dithiolan-2-yl)-3-cephem-4-carboxylate.

11. A method of producing antimicrobial activity in a subject in need of such treatment which comprises administering to said subject an antimicrobial effective amount of the pharmaceutical composition of claim 6.

12. The method of claim 11, wherein said pharmaceutical composition contains (Z)-7-[2-(2-amino-4-thiazolyl)-2-(hydroxyimino)acetamido]-3-(1,3-dithiolan-2-yl)-3-cephem-4-carboxylic acid.

13. The method of claim 11, wherein said pharmaceutical composition contains 1-acetoxyethyl (Z)-7-[2-(2-amino-4-thiazolyl)-2-(hydroxyimino)acetamido]-3-(1,3-dithiolan-2-yl)-3-cephem-4-carboxylate.

14. The method of claim 11, wherein said pharmaceutical composition contains 1-pivaroyloxymethyl (Z)-7-[2-(2-amino-4-thiazolyl)-2-(hydroxyimino)acetamido]-3-(1,3-dithiolan-2-yl)-3-cephem-4-carboxylate.

15. The method of claim 11, wherein said pharmaceutical composition contains 1-cyclohexylacetoxyethyl (Z)-7-[2-(2-amino-4-thiazolyl)-2-(hydroxyimino)acetamido]-3-(1,3-dithiolan-2-yl)-3-cephem-4-carboxylate.

* * * * *